(12) United States Patent
Waber

(10) Patent No.: US 8,993,986 B2
(45) Date of Patent: Mar. 31, 2015

(54) ELECTRON BEAM EMITTER WITH A COOLING FLANGE, AND A METHOD OF COOLING AN ELECTRON BEAM EMITTER

(75) Inventor: Toni Waber, Aefligen (CH)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 14/126,131

(22) PCT Filed: Jun. 27, 2012

(86) PCT No.: PCT/EP2012/062453
§ 371 (c)(1),
(2), (4) Date: Dec. 13, 2013

(87) PCT Pub. No.: WO2013/004564
PCT Pub. Date: Jan. 10, 2013

(65) Prior Publication Data
US 2014/0103228 A1    Apr. 17, 2014

Related U.S. Application Data

(60) Provisional application No. 61/525,127, filed on Aug. 18, 2011.

(30) Foreign Application Priority Data

Jul. 4, 2011  (SE) .................................... 1100518-8

(51) Int. Cl.
*H01J 1/42* (2006.01)
*A61L 2/08* (2006.01)
*H01J 33/00* (2006.01)

(52) U.S. Cl.
CPC . *H01J 1/42* (2013.01); *A61L 2/087* (2013.01); *H01J 33/00* (2013.01)
USPC .................... 250/492.3; 250/423 R; 250/427; 250/435; 250/205

(58) Field of Classification Search
USPC ................... 250/492.3, 423 R, 427, 435, 205
See application file for complete search history.

(56) References Cited

U.S. PATENT DOCUMENTS

| | | | |
|---|---|---|---|
| 4,574,178 A * | 3/1986 | Spruck ..................... | 219/121.27 |
| 4,777,370 A * | 10/1988 | Pigache et al. ............ | 250/423 R |
| 2004/0109539 A1 | 6/2004 | Apel et al. | |
| 2007/0114432 A1* | 5/2007 | Kristiansson et al. ........ | 250/397 |
| 2012/0043935 A1 | 2/2012 | Dyer et al. | |

FOREIGN PATENT DOCUMENTS

| | | |
|---|---|---|
| CN | 201 674 338 U | 12/2010 |
| EP | 0 228 318 A1 | 7/1987 |
| GB | 2 166 284 A | 4/1986 |
| WO | WO 2007/050007 A1 | 5/2007 |

OTHER PUBLICATIONS

International Search Report (PCT/ISA/210) mailed on Nov. 30, 2012, by the European Patent Office as the International Searching Authority for International Application No. PCT/EP2012/062453.
Swedish Search Report for SE 1100518-8 dated Jan. 9, 2012.

* cited by examiner

*Primary Examiner* — David Porta
*Assistant Examiner* — Meenakshi Sahu
(74) *Attorney, Agent, or Firm* — Buchanan Ingersoll & Rooney PC

(57) ABSTRACT

An electron beam emitter comprises a housing enclosing a cathode capable of emitting electrons within the housing and a window for allowing the emitted electrons to exit the housing, wherein the housing has an opening adapted to be at least partly engaged with a high voltage connector assembly, the assembly being adapted to connect the cathode to a power supply, the electron beam emitter further comprising a cooling flange surrounding the opening and having an interior channel extending between an inlet port and an outlet port for receiving cooling fluid for cooling the high voltage connector assembly. The invention further relates to a method of cooling an electron beam device.

13 Claims, 4 Drawing Sheets

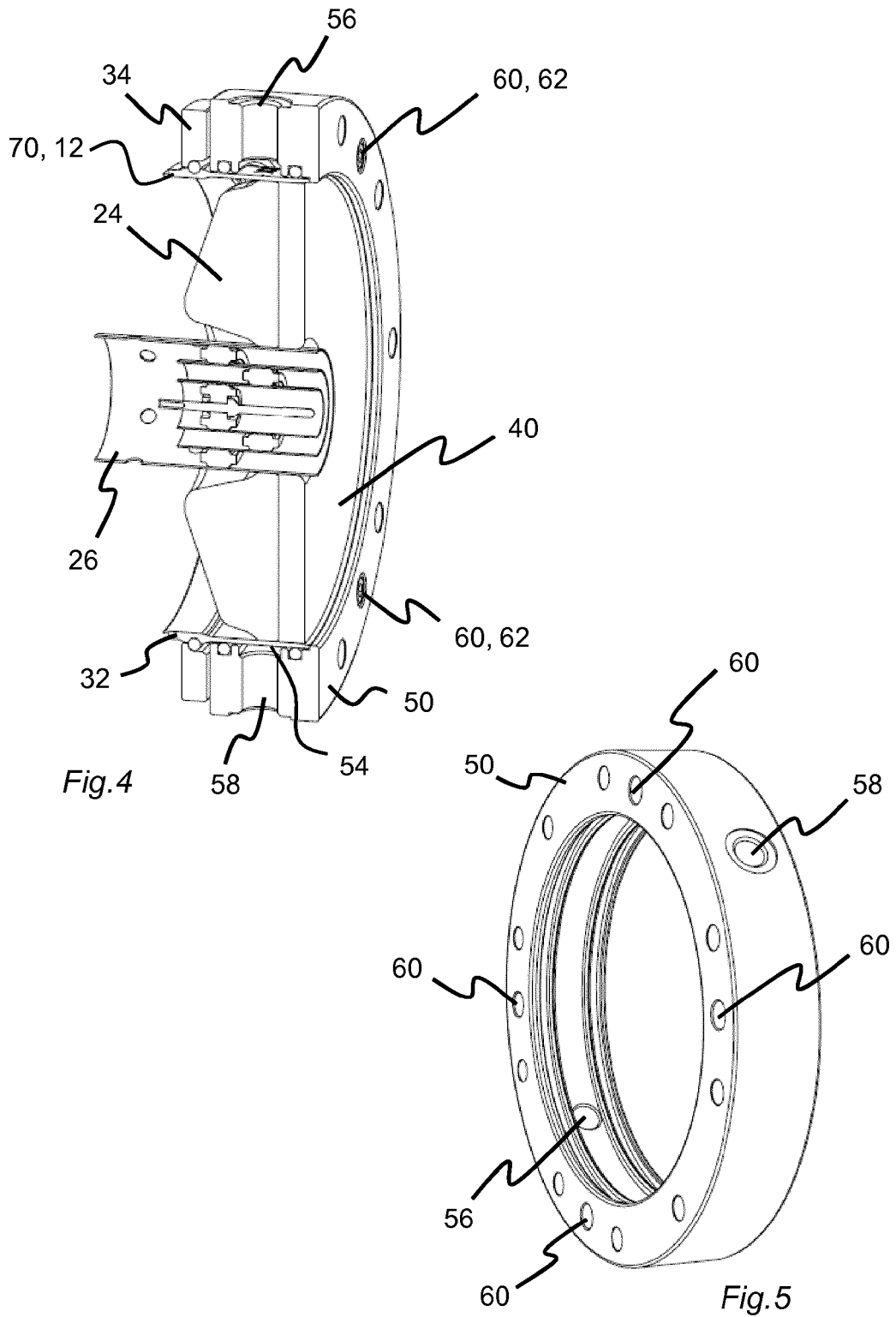

US 8,993,986 B2

ELECTRON BEAM EMITTER WITH A COOLING FLANGE, AND A METHOD OF COOLING AN ELECTRON BEAM EMITTER

FIELD OF THE INVENTION

The present invention relates to an electron beam emitter. More particularly, the present invention relates to an electron beam emitter having a cooling flange for reducing the temperature of the electron beam emitter. The invention further relates to a method of cooling an electron beam device.

BACKGROUND ART

Electron beam emitters have been known for a long time and different applications are continuously arising due to the number of advantages over other techniques.

In e.g. liquid food packaging electron beam irradiation has been considered as a promising alternative for sterilizing purposes, for which wet chemistry involving hydrogen peroxide has been the traditional technical platform. However electron beam emitters may be utilized to provide sufficient sterilization of the packaging material thus eliminating the negative consequences of wet chemistry within the packaging machine.

Different issues need to be considered when dealing with electron beam emitters, of which excessive heat is one important aspect. The electron beam emitter, commonly including a main body enclosing an electrically powered cathode and an exit window, will provide a cloud or beam of emitted electrons when activated. As a result of the scattered electrons, and a high temperature electron-generating filament inside the electron beam emitter, the heat dissipated within the main body of the electron beam emitter will be high and so will the temperature within the main body.

The exit window may for this reason be provided with external cooling for improving the stability and operating life time of the exit window.

However, there is also a need for reducing the temperature at the connector area, i.e. at the location where the cathode is connected to the power supply. This is due to the fact that excessive heat is transferred from the main body towards the connector area. At this position, the temperature should not exceed 70° C. and preferably stay below 50° C. in order to provide optimal performance of the connector area. To provide the necessary cooling a simple, low-cost cooling solution is needed.

There is thus a need for an improved electron beam emitter which is capable of providing efficient cooling of the connector area. Further, there is also a need for an electron beam emitter for which the connector area cooling is provided by means of a less complex and more cost effective solution.

SUMMARY OF THE INVENTION

Therefore, an object of the invention has been to provide a device for electron beam irradiation in which the above mentioned considerations have been taken into account and solved.

In an embodiment of the invention an electron beam emitter comprises a housing enclosing a cathode which is capable of emitting electrons within said housing and a window for allowing said emitted electrons to exit said housing. Said housing has an opening adapted to be at least partly engaged with a high voltage connector assembly, said assembly being adapted to connect said cathode to a power supply. Said electron beam emitter further comprising a cooling flange surrounding said opening and having an interior channel extending between an inlet port and an outlet port for receiving cooling fluid for cooling said high voltage connector assembly.

The interior channel of said cooling flange may be a circular loop which is advantageous in that the cooling flange may provide improved cooling of the connecting area of the electron beam emitter.

The cross section of said cooling flange is essentially U-shaped such that said interior channel of said cooling flange is sealed by the outer surface of the housing. Hence, efficient cooling is provided since the wall of the housing is in direct contact with the cooling fluid flowing within said cooling flange.

The cooling flange may comprise scalings for providing a fluid tight seal between said cooling flange and the outer surface of the housing. Hence, possible leakage of cooling fluid is prevented.

The inlet port and the outlet port may be arranged on opposite sides of said cooling flange, which is advantageous in that cooling fluid is allowed to flow evenly in both directions from the inlet port to the outlet port.

The opening may have a circular shape, and the cooling flange may have a ring shape. Hence there will be no sharp corners in the interior channel of the cooling flange which is advantageous in that there will be no undesired turbulence in the flow of the cooling fluid.

The opening may be arranged on an axial edge of said housing, which facilitates the mounting and connecting procedure of the power supply to the electron beam emitter housing.

An electrical insulator may be arranged between said housing and said cathode at said opening, wherein the electrical insulator may be made of a ceramic material.

The invention further relates to a filling machine capable of providing carton-based packages enclosing liquid food, comprising an electron beam emitter as described above.

The invention further relates to a method for cooling an electron beam emitter comprising a housing enclosing a cathode capable of emitting electrons within said housing and a window for allowing said emitted electrons to exit said housing. Said housing has an opening adapted to be at least partly engaged with a high voltage connector assembly, said assembly being adapted to connect said cathode to a power supply. The method comprises the steps of providing a cooling flange surrounding said opening and having an interior channel extending between an inlet port and an outlet port, and supplying cooling fluid to said inlet port for cooling said high voltage connector assembly.

The invention further relates to a method for sterilizing a carton-based packaging material in a filling machine by means of an electron beam emitter comprising said method.

BRIEF DESCRIPTION OF THE DRAWINGS

Hereinafter, the invention will be described with reference to the appended drawings, wherein:

FIG. 4 is an isometric view of portions of the connector assembly and the housing shown in FIG. 3 in an assembled state;

FIG. 5 is an isometric view of a cooling flange according to an embodiment; and

DESCRIPTION OF EMBODIMENTS

Figure 1:
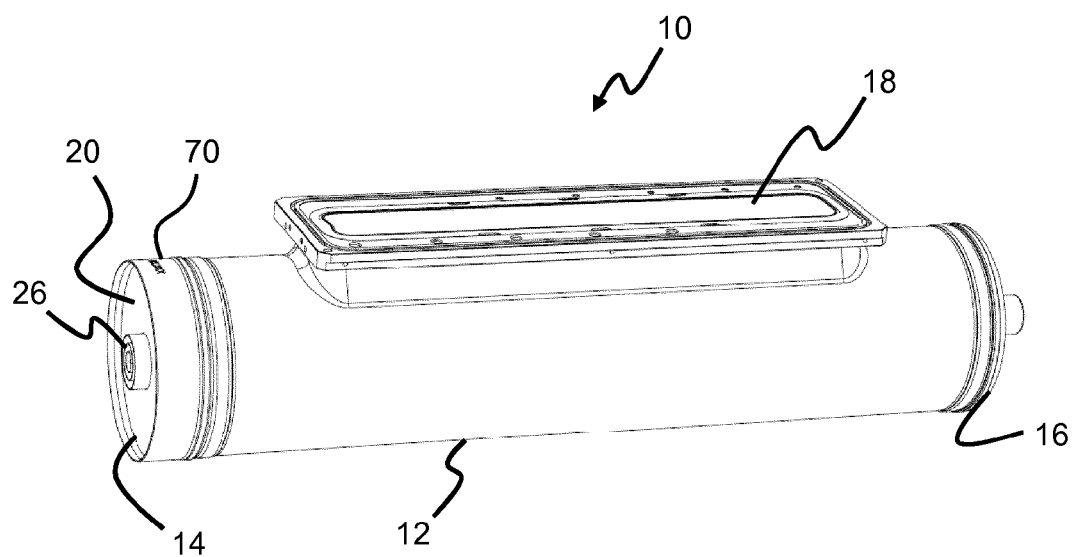
FIG. 1 is an isometric view of an electron beam emitter according to an embodiment.

With reference to FIG. 1 an electron beam emitter 10 is shown. The electron beam emitter has a housing 12 extending between a first end 14 and a second end 16. The housing 12, having a tubular shape and forming a main body of the electron beam emitter 10, is provided with an electron exit window 18 extending along the longitudinal axis of the housing 12.

The first end 14 of the housing 12 has an opening 20 through which a cathode 22 (shown in FIG. 2) may be inserted and aligned laterally with the electron exit window 18. The opening 20 is adapted to be engaged with a high voltage connector assembly of which an electrically insulating disc 24 is inserted into the opening 20 and positioned between the periphery of the housing 12 and a male connector part 26 of the connector assembly. The male connector part 26 is in one end connected to the cathode 22 and in the other end connected to a female connector part 38 (shown in FIG. 3), said female connector part 38 being connected to a power supply. The insulating disc 24 electrically insulates the cathode 22.

Figure 2:
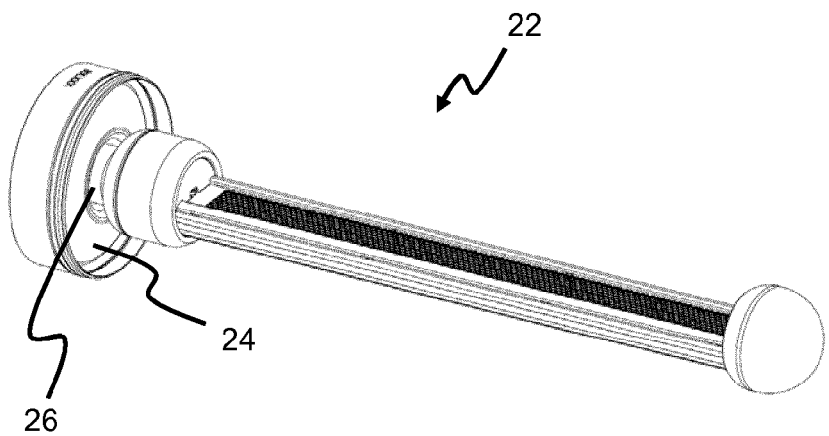
FIG. 2 is an isometric view of a cathode of an electron beam emitter according to an embodiment.

With reference to FIG. 2, the cathode 22 and some parts of the high voltage connector assembly is shown in further detail. The electrically insulating material 24, having a ring shape, surrounds the male connector part 26. The cathode 22 is extending within the housing 12 and has a length which corresponds to the length of the exit window 18 of the housing 12. The cathode 22 includes a number of components which are well known in the art, such as a filament, a control grid, etc.

Figure 3:
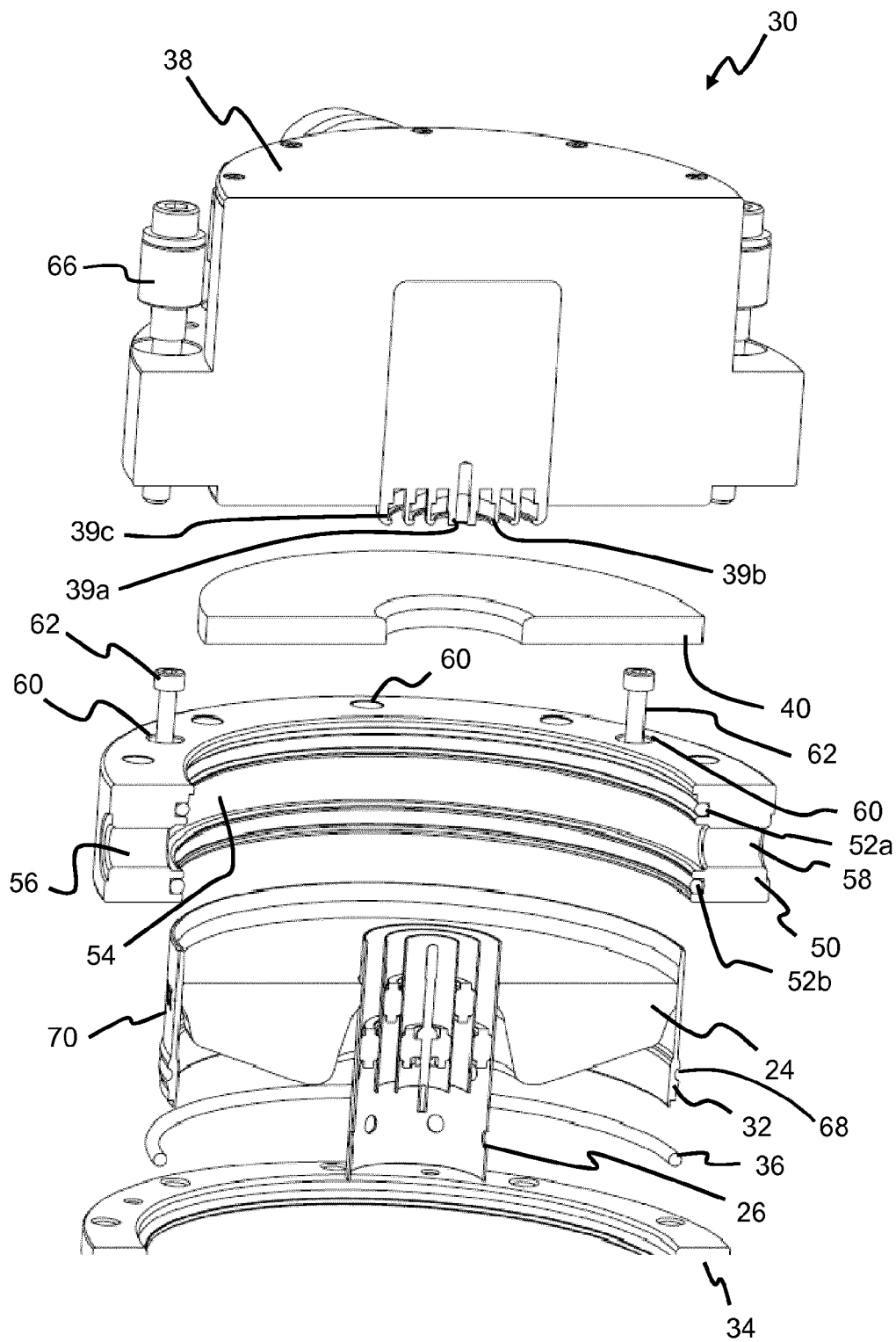
FIG. 3 is an exploded isometric cross sectional view of a connector assembly of an electron beam emitter according to an embodiment together with a portion of the housing.

Now referring to FIG. 3 and FIG. 4, the high voltage connector assembly 30 of an electron beam emitter is shown. The connector assembly 30 is provided to the first end 14 of the electron beam emitter 10 shown in FIG. 1 and includes a number of components which form the first end 14.

The male connector part 26 is surrounded by the ring shaped disc 24 of electrically insulating material, and attached to the wall 32 of the housing 12 by means of a circular flange 34. Preferably, a ring 36 made of stainless steel is provided to hold the flange 34 in place on the housing 12. In fact, the ring 36 cooperates with a groove 68 in the housing 12 to form an end stop for the flange 34. The ring shaped disc 24 is preferably made of a ceramic material, for example comprising $Al_2O_3$. The housing 12 is made of stainless steel, but has an end portion 70 preferably made of an alloy comprising iron (Fe), nickel (Ni) and copper (Co), which has a thermal coefficient between the ceramic material and the stainless steel.

The female connector part 38 is adapted to be electrically connected to the male connector part 26 and may include different connectors 39a, 39b, 39c, for connecting to different parts of the cathode 22. The female connector part 38 is connected to a power supply (not shown) through a cable (not shown). For example, a first connector 39a may provide a voltage to a filament (not shown), a second connector 39b may provide a voltage to a control grid (not shown), and a third connector 39c may provide a voltage to the cathode body (not shown). However different connector configurations may also be utilized in order to provide adequate functionality of the cathode.

A spacer 40 is further arranged between the female connector part 38 and the ceramic disc 24.

A cooling flange 50 is provided at the exterior surface of the wall 32 of the portion 70 of the housing 12, preferably being axially aligned with the interface of the male connector part 26 and the connectors 39a, 39b, 39c as well as with the ceramic disc 24. The cooling flange 50 has a circular ring shape and is sealed against the wall 32 by means of two O-rings 52a, 52b.

The cooling flange 50 has an angular U-shaped cross section such that a rectangular interior channel 54 is formed between the interior walls of the cooling flange 50 and the wall 32 of the portion 70 of the housing 12. The cooling flange 50 is further provided with an inlet port 56 and an outlet port 58. The inlet port 56 and the outlet port 58 are preferably arranged on opposite sides of the cooling flange 50 such that cooling fluid, e.g. water, may enter the interior channel 54 of the cooling flange 50 and flow in opposite directions towards the outlet port 58 where the cooling fluid is allowed to exit the cooling flange 50. Preferably the inlet port 56 and the outlet port 58 are connected by means of a closed circulation system, including e.g. fluid line, a pump, a heat exchanger, etc. The circulation system may thus be arranged remote of the electron beam emitter and may consequently form a part of already existing cooling systems depending on the particular application and implementation of the electron beam emitter.

The cooling flange 50 has a number of receiving bores 60, extending axially through the cooling flange 50 outside the interior channel 54. The receiving bores 60 are configured to receive bolts 62 or other fasteners for securing the cooling flange 50 to threaded bores in flange 34. The female connector part 38 is provided with bolts 66 for securing it to the threaded bores in flange 34, and consequently securing it also to the housing 12. The bolts 66 of the female connector part 38 are extending through some of the bores 60 in the flange 34, which bores are provided without threading.

With reference to FIG. 5 the cooling flange 50 is shown in further detail. Here, the cooling flange 50 has a circular ring shape such that is may be fitted with a cylindrical housing of an electron beam emitter. Other shapes may also be used, e.g. rectangular etc, as long as the inner dimensions of the cooling flange 50 corresponds to the outer dimensions of the first end 14 of the housing 12. The cooling flange 50 may be made of various materials, such as for example stainless steel or for example aluminium with a corrosion protection coating. Further, two grooves 64, 65 are provided adjacent to the interior channel 54 for receiving the O-rings 52a, 52b shown in FIG. 3 in order to prevent cooling fluid to leak out.

Figure 6:
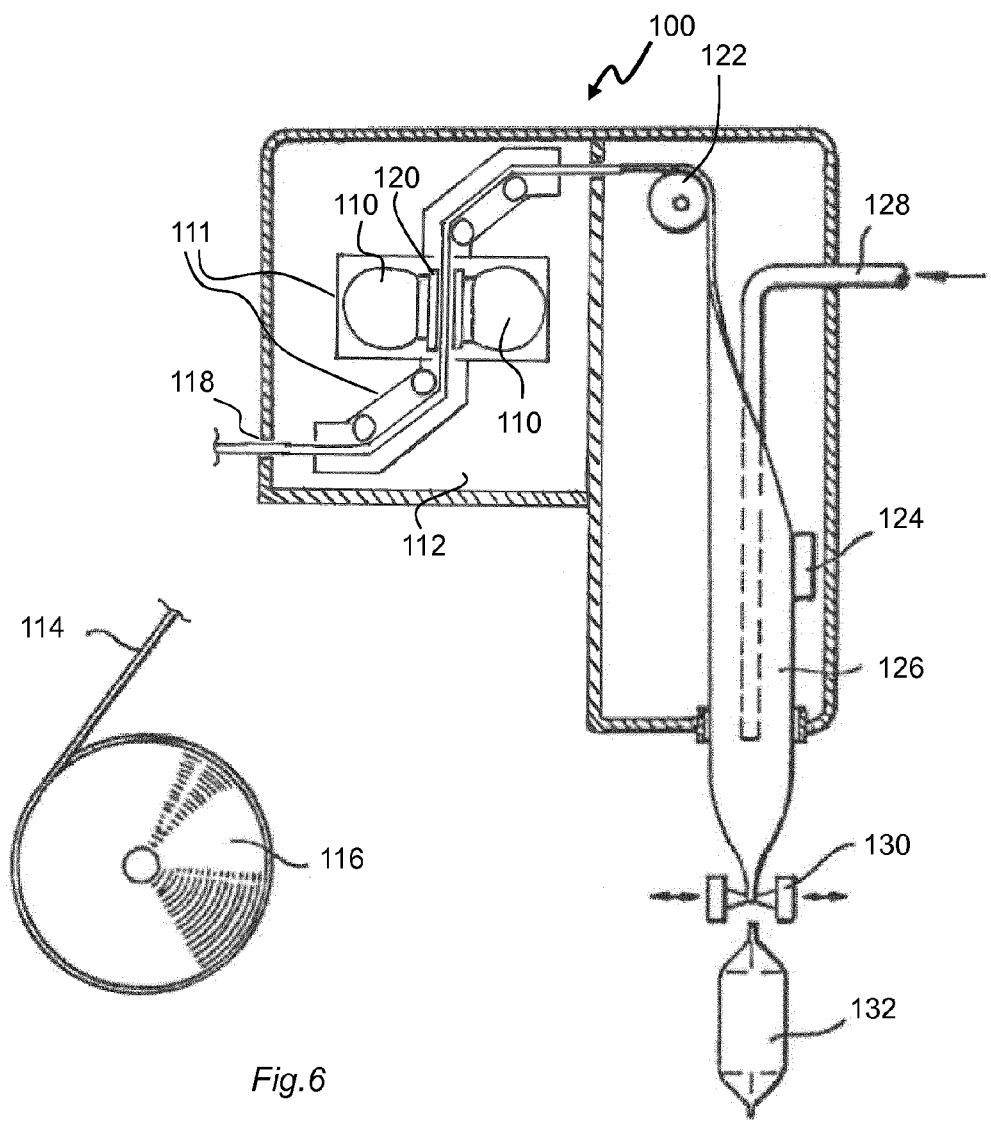
FIG. 6 is a side view of a filling machine including an electron beam emitter according to an embodiment. The drawing is not according to scale.

With reference to FIG. 6 a filling machine 100 is shown, utilizing two oppositely directed electron beam emitters 110. The electron beam emitters 110 are constructed according to what has been described with reference to FIGS. 1 to 5. When electron beam emitters 110 are employed for sterilizing packaging material in automatic packaging machines, they can, for instance, be arranged in the manner illustrated in FIG. 6 which illustrates a sterile chamber 112 into which a packaging material web 114 which is unwound from a magazine reel 116 is fed through a passage 118. In the sterile chamber 112, a sterile atmosphere is maintained and, in order that no infected air can penetrate in through the passage 118, a slight excess pressure may be maintained within the sterile chamber 112. The web 114 introduced into the sterile chamber 112 is caused to pass, in this case, the electron beam emitters 110 whose exit window 120 are aimed towards the inside and outside surfaces of the packaging material web 114. The electron beam emitters 110 are shielded off from the environment by an essentially S-formed x-ray shield 111. On passage of the packaging material web 114 past the electron beam emitters 110, the surfaces of the web 114 is affected by electron beams of energy-enriched electrons from the emitters 110, whereupon the interior and exterior sides of the web is sterilized. The web is thereafter led into a tubeforming section, whereby the web is passed over a bending roller 122 and formed into a tube in that the longitudinal edges of the web 114 are united to one another and sealed by means of a longitudinal sealing device 124. The tube 126 of sterilized packaging material is filled with sterile contents through the supply conduit 128, whereafter the tube 126 is discharged out of the sterile chamber 112 and is divided by means of sealing devices 130 into individual packaging containers 132 by repeated transverse seals transversely of the longitudinal direction of the tube 126. The formed packaging units 132 can then be separated into individual packaging containers by means of incisions in the sealing zones, and possibly be formed by folding or other means into parallelepipedic packages or packages of other configuration.

Although specific embodiments have been described it should be appreciated that various modifications may be made to the electron beam emitter without departing from the scope as defined in the accompanying claims.

The invention claimed is:

1. An electron beam emitter comprising a housing enclosing a cathode configured to emit electrons within said housing and a window for allowing said emitted electrons to exit said housing wherein said housing has an opening adapted to be at least partly engaged with a high voltage connector assembly, said housing possessing an outer surface, said assembly being adapted to connect said cathode to a power supply, said electron beam emitter further comprising
a cooling flange surrounding said opening and having an interior channel extending between an inlet port and an outlet port for receiving cooling fluid for cooling said high voltage connector assembly,
wherein the cooling flange is located on the outer surface of the housing, and
wherein the interior channel of the cooling flange is formed by interior walls of the cooling flange and the outer surface of the housing.

2. The electron beam emitter according to claim 1, wherein said interior channel of said cooling flange is a circular loop.

3. The electron beam emitter according to claim 2, wherein the cross section of said cooling flange is essentially U-shaped such that said interior channel of said cooling flange is sealed by the outer surface of the housing.

4. The electron beam emitter according to claim 3, wherein said cooling flange comprises sealings for providing a fluid tight seal between said cooling flange and the outer surface of the housing.

5. The electron beam emitter according to claim 1, wherein said inlet port and said outlet port are arranged on opposite sides of said cooling flange.

6. The electron beam emitter according to claim 1, wherein said opening has a circular shape, and wherein said cooling flange has a ring shape.

7. The electron beam emitter according to claim 1, wherein said opening is arranged on an axial edge of said housing.

8. The electron beam emitter according to claim 1, wherein an electrical insulator is arranged between said housing and said cathode at said opening.

9. The electron beam emitter according to claim 8, wherein said electrical insulator is made of a ceramic material.

10. A filling machine configured to provide carton-based packages enclosing liquid food, comprising an electron beam emitter according to claim 1.

11. A method for cooling an electron beam emitter comprising a housing enclosing a cathode configured to emit electrons within said housing and a window for allowing said emitted electrons to exit said housing, wherein said housing has an opening adapted to be at least partly engaged with a high voltage connector assembly, said housing possessing an outer surface, said assembly being adapted to connect said cathode to a power supply,
said method comprising:
supplying cooling fluid to an inlet port of a cooling flange located on the outer surface of the housing and surrounding said opening, the cooling flange including an interior channel extending between the inlet port and an outlet port, wherein the interior channel of the cooling flange is formed by interior walls of the cooling flange and the outer surface of the housing; and
circulating the cooling fluid supplied to the inlet port through the interior channel of the cooling flange to cool the high voltage connector assembly.

12. A method for sterilizing a carton-based packaging material in a filling machine by means of an electron beam emitter, comprising the method according to claim 11.

13. The electron beam emitter according to claim 1, wherein the housing and the cathode each possesses a respective longitudinal axis, the longitudinal axis of the cathode being axially aligned with the longitudinal axis of the housing where the cooling flange is located.

* * * * *